(12) United States Patent
Zhang

(10) Patent No.: US 7,005,140 B2
(45) Date of Patent: Feb. 28, 2006

(54) LIPID PARTICLES HAVING ASYMMETRIC LIPID COATING AND METHOD OF PREPARING SAME

(75) Inventor: Yuanpeng Zhang, Cupertino, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 10/814,703

(22) Filed: Mar. 30, 2004

(65) Prior Publication Data

US 2004/0191306 A1   Sep. 30, 2004

Related U.S. Application Data

(60) Provisional application No. 60/519,905, filed on Nov. 14, 2003, provisional application No. 60/459,305, filed on Mar. 31, 2003.

(51) Int. Cl.
A61K 9/127 (2006.01)
A61K 48/00 (2006.01)

(52) U.S. Cl. ........................... 424/450; 514/44

(58) Field of Classification Search ............... 424/450; 514/44
See application file for complete search history.

(56) References Cited

U.S. PATENT DOCUMENTS

| | | | |
|---|---|---|---|
| 4,394,448 A | 7/1983 | Szoka, Jr. et al. | |
| 5,013,556 A | 5/1991 | Woodle et al. | |
| 5,283,185 A | 2/1994 | Epand et al. | |
| 5,395,619 A | 3/1995 | Zalipsky et al. | |
| 5,416,203 A | 5/1995 | Letsinger et al. | |
| 5,851,818 A | 12/1998 | Huang et al. | |
| 5,891,468 A | 4/1999 | Martin et al. | |
| 5,972,600 A | 10/1999 | Szoka, Jr. et al. | |
| 6,056,973 A | 5/2000 | Allen et al. | |
| 6,180,134 B1 | 1/2001 | Zalipsky et al. | |
| 6,210,707 B1 | 4/2001 | Papahadjopoulos et al. | |
| 6,287,591 B1 * | 9/2001 | Semple et al. | 424/450 |
| 2003/0091621 A1 * | 5/2003 | Tardi et al. | 424/450 |

FOREIGN PATENT DOCUMENTS

| | | |
|---|---|---|
| WO | WO 95/27478 A1 | 10/1995 |
| WO | WO 97/07784 A2 | 3/1997 |
| WO | WO 98/51278 A2 | 11/1998 |
| WO | WO 02/43769 A2 | 6/2002 |

OTHER PUBLICATIONS

Felgner et al., *Proc. Natl. Acad Sci USA*, 84(21):7413-7417, Nov. 1987. "Lipofection: a highly efficient, lipid-mediated DNA-transfection procedure".
Gershon, H. et al., *Biochemistry*, 32(28):7143-7151, Jul. 20, 1993. "Mode of formation and structural features of DNA-cationic liposome complexes used for transfection".
Guo, L., et al., *Journal of Liposome Research*, 3(1):51-70, 1993.
Malone, R.W., et al., *Proc. Natl. Acad Sci USA*, 86:6077-6081, Aug. 1989. Cationic liposome-mediated RNA transfection.
Straubinger & Papahadjopulos, *Methods of Enzmology*, 101: 512-527, 1983. "Liposomes as carriers for intracellular delivery of nucleic acids".
Szoka Jr., Francis., et al., *Ann Rev Biophys. Bioeng*, 9:467, 1980. Comparative properties and methods of preparation of lipid vesicles (liposomes).
Zelphati, O. et al., *Proc. Natl. Acad Sci USA*, 93(21):11493-8, Oct. 15, 1996. Mechanism of oligonucleotide release from cationic liposomes.
PCT Search Report dated Sep. 27, 2004, for corresponding patent application No. PCT/US2004/009809.

* cited by examiner

*Primary Examiner*—James Ketter
*Assistant Examiner*—Tara L Garvey
(74) *Attorney, Agent, or Firm*—Michael J. Atkins

(57) ABSTRACT

A method of preparing lipid particles having an asymmetric lipid coating is described. The lipid composition of the outer lipid coating of the particles varies from the inner to outer surfaces. The asymmetric lipid particles are formed by preparing a lipid composition containing a charged lipid and a therapeutic agent, where the particles each have an outer lipid coating with an external lipid leaflet and an internal lipid structure. The particles are then incubated under conditions effective to remove the charged lipid from the external lipid leaflet, thus rendering the lipid coating asymmetric. The particles have the ability to their regain surface charge via translocation of the lipids.

18 Claims, 9 Drawing Sheets

LIPID PARTICLES HAVING ASYMMETRIC LIPID COATING AND METHOD OF PREPARING SAME

This application claims the benefit of U.S. Provisional Application No. 60/519,905, filed Nov. 14, 2003 and of U.S. Provisional Application No. 60/459,305, filed Mar. 31, 2003, both of which are incorporated herein by reference in their entirety.

FIELD OF THE INVENTION

The present invention relates to a lipid particle composition having an asymmetric lipid coating, for use in delivery of therapeutic agents to a person, and more specifically, to a cell.

BACKGROUND OF THE INVENTION

Lipid vesicles, or liposomes, have demonstrated utility for delivering therapeutic agents and diagnostic agents to target tissues and organs. Lipid vesicles have an aqueous interior enclosed by one or more lipid bilayers, where the therapeutic agent is entrapped in the aqueous interior spaces or within the lipid bilayer. Thus, both water-soluble and water-insoluble drugs can be transported by lipid vesicles within the aqueous spaces and the lipid bilayer, respectively.

The action of many drugs involves their direct interaction with sites inside the cell. For action, the drug must pass through the cell membrane to reach the cytoplasm. Success in achieving intracellular delivery of a liposome-entrapped agent has been limited for a variety of reasons. One reason is that liposomes, after systemic administration to the bloodstream, are rapidly removed from circulation by the reticuloendothelial system. Another reason is the inherent difficulty in delivering a molecule, in particular a large and/or a charged molecule, into the cellular cytoplasm and/or the nucleus.

The limitation of rapid uptake by the reticuloendothelial system has largely been overcome by the addition of a hydrophilic polymer surface coating on the liposomes to mask the vesicle from recognition and uptake by the reticuloendothelial system. The extended blood circulation lifetime of liposome having a coating of polyethyleneglycol (PEG) polymer chains (U.S. Pat. No. 5,013,556) allows for a greater opportunity for uptake by a cell.

Delivery of charged molecules intracellularly remains a technical challenge. In particular, delivery of nucleic acids, both DNA and RNA, has been challenging, due to the charge and size of the molecules. Proteins, peptides, and charged drug compounds involve the same technical hurdle of transport across a cell membrane. One approach to delivery of negatively charged agents, particularly nucleic acids fragments for gene therapy, has been to complex the DNA or RNA with a cationic lipid. Electrostatic interaction of the cationic lipid with the nucleic acid permits formation of lipid-nucleic acid particles in a size range suitable for in vivo administration. The positively charged cationic lipid on the outer particle surfaces is beneficial for interaction with negatively-charged cellular membranes, to promote fusion or uptake of the lipid-nucleic acid particles into the cell.

However, the presence of the positive charge on the external surface of lipid particles prepared with cationic lipids is detrimental to the goal of achieving a long blood circulation lifetime for widespread biodistribution. The charge on the particles causes immediate binding with the tissue surfaces at or near the site of administration, substantially limiting the availability of particles for circulation and distribution to the target site. It would be desirable to design a lipid vesicle composition that is neutral upon administration to permit biodistribution, yet that is charged after a period of time, i.e., after biodistribution of the particles, to permit interaction with cell membranes for binding and intracellular delivery of the entrapped agent.

SUMMARY OF THE INVENTION

Accordingly, it is an object of the invention to provide a lipid particle composition that includes a charged lipid for interaction with a charged therapeutic agent, yet which bears minimal external surface charge after formation.

It is another object of the invention to provide a lipid particle composition that includes a charged lipid and has minimal external surface charge after particle formation, but that is capable of developing a charge over time, such as during incubation at physiological temperature.

In one aspect, the invention includes a method of preparing lipid particles having an external lipid coating. The method comprises preparing lipid particles composed of (i) a lipid composition containing a charged lipid and (ii) a therapeutic agent. The particles each have an outer lipid coating having an external lipid leaflet and an internal lipid structure. The particles are then incubated under conditions effective to remove the charged lipid from the external lipid leaflet.

In one embodiment, the lipid particles are composed of a lipid composition containing at least one cationic lipid.

In another embodiment, step of preparing comprises (i) forming lipid vesicles composed of the lipid composition and (ii) complexing the lipid vesicles with the therapeutic agent.

Incubation of the lipid particles, in one embodiment, involves incubation in a medium containing uncharged lipid vesicles. In another embodiment, a lipid-polymer-ligand conjugate can be added to the incubation medium. In other embodiment, the incubation medium can further include a lipid derivatized with a hydrophilic polymer. An exemplary lipid derivatized with a hydrophilic polymer is a phospholipid derivatized with polyethyleneglycol.

In other embodiments, incubation of the particles is conducted at a temperature of less than about 15° C. and/or for a time of greater than about 5 hours.

In one embodiment, the lipid particles are liposomes.

In still other embodiments, the lipid particles are prepared to have an entrapped therapeutic agent selected from the group consisting of a charged drug, a protein, a peptide, and a nucleic acid.

In another aspect, the invention includes a composition comprising lipid particles having a lipid coating comprised of an outer lipid leaflet and an inner lipid structure. The lipid coating is formed of a lipid composition (i) comprising a charged lipid and (ii) having a gel-crystalline phase transition temperature, where the lipid particles have little or no appreciable charge at a temperature lower than the lipid composition's phase transition temperature, but have a measurable charge after incubation at a temperature above the phase transition temperature.

In one embodiment, the lipid composition has a phase transition of between about 34–38° C.

In yet another aspect, the invention includes a method of preparing lipid particles having an asymmetric charged lipid composition in its outer lipid coating prior to in vivo administration. The method includes preparing lipid particles comprised of (i) a lipid composition containing a charged lipid and (ii) a therapeutic agent, where the particles each have an outer lipid coating having an external lipid leaflet and an internal lipid structure. The particles are incubated under conditions effective to remove charged lipids from the external lipid leaflet.

In one embodiment, the incubation is done by incubating at a temperature of less than about 15° C. In another embodiment, the incubation period is for a time of greater than about 5 hours. In another embodiment, the incubating medium is comprised of neutral lipid vesicles.

These and other objects and features of the invention will be more fully appreciated when the following detailed description of the invention is read in conjunction with the accompanying drawings.

DETAILED DESCRIPTION OF THE INVENTION

I. Definitions

"Lipid particle" as used herein intends particles of any shape or size that have at least one lipid bilayer. That is, the term includes unilamellar, plurilamellar, and multilamellar vesicles. In some particles, portions of the particle may be unilamellar and other portions may be multilamellar. The particles may be spherical or may be more globular in shape. Included within the term "lipid particle" are liposomes as well as complexes of lipids with other particle components. The particle may have a defined aqueous space, i.e., a liposome, or may have pockets or regions of aqueous space(s), i.e., lipid complexes.

Abbreviations: DMTAP: 1,2-dimyristoyl-3-trimethylammonium-propane; DOPE: dioleoylphosphatidylethanolamine; PEG: polyethyleneglycol; DS: distearoyl; mPEG-DS: methoxy(polyethyleneglycol)-distearoyl.

II. Lipid Particles and Method of Preparation

Figure 1A:
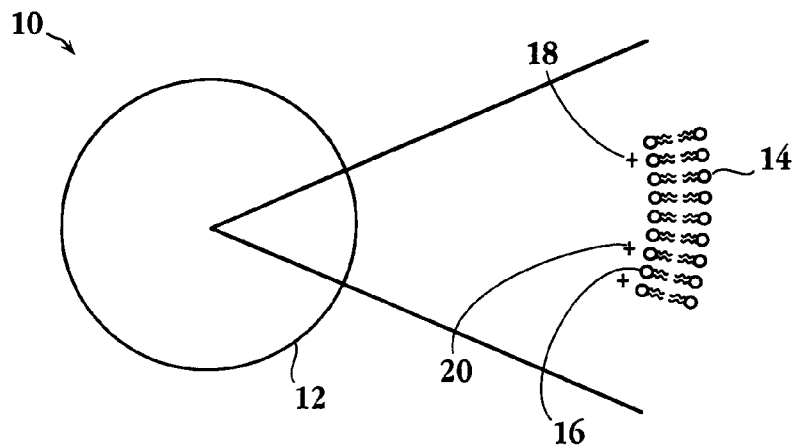
FIGS. 1A–1E are illustrations of lipid particles described herein.

In one aspect, the invention relates to a method for preparing lipid particles that have an external lipid coating having an outer surface and an inner lipid portion, and a compositional gradient across the lipid coating extending between the outer surface and inner lipid region. Such particles having a compositional gradient across all or a portion of the lipid coating have what is referred to as an asymmetric lipid composition, as will now be illustrated in FIGS. 1A–1E, where idealized illustrations of such lipid particles are shown. FIG. 1A shows a unilamellar lipid particle 10 having a single outer lipid coating 12. A portion of the lipid coating is shown in exploded view to better illustrate the arrangement of the lipids. The coating is comprised of an external coating surface 14 and an internal coating surface 16. As illustrated here, the coating takes the form of a lipid bilayer; however this illustration is idealized and the lipid coating may have a more complex arrangement of lipids. The external coating surface corresponds to an outer lipid leaflet of the coating, where the polar head groups of the lipids in the leaflet are oriented for contact with the external bulk medium in which the particles are suspended. The internal coating surface corresponds to an inner lipid structure, which can be a lipid leaflet or can be a more complex arrangement of lipids, where the polar head groups of the lipids in the inner leaflet are oriented for contact within the aqueous space of the particle. The outer lipid leaflet has a low or minimal charge, by virtue of being comprised predominantly of lipids bearing no positive (cationic) or negative (anionic) charge, for example, neutral vesicle-forming lipids or other neutral lipids. In a preferred embodiment, the outer lipid leaflet is comprised of neutral or anionic lipids; that is, the outer lipid leaflet contains little or no appreciable cationic charge due to the presence of cationic lipids. The inner lipid structure is comprised of charged lipids. This feature is illustrated in FIG. 1A by the indication of positively charged lipids at 18, 20 in the inner lipid structure that provide a positive charge on the internal coating surface. For this lipid particle having a unilamellar lipid coating, the difference in lipid composition between the inner and outer lipid leaflets form what is referred to herein as an asymmetric lipid coating. More specifically, the difference in charged lipid composition across the thickness of the outer lipid coating is referred to as an asymmetric outer lipid coating.

Figure 1B:
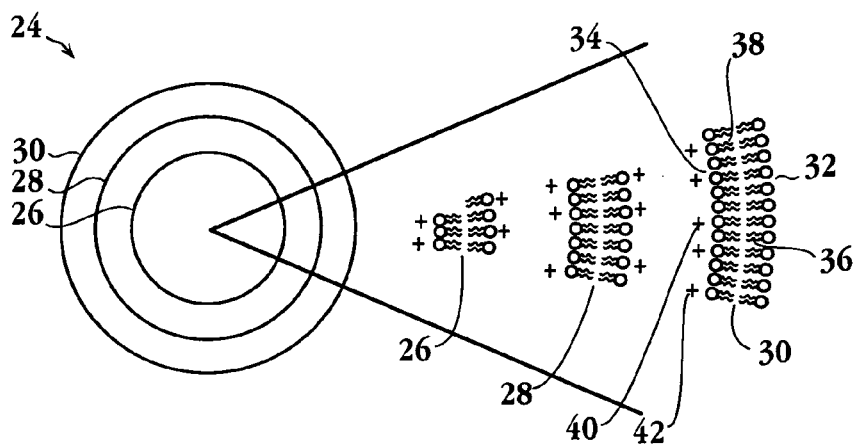
Figure 1C:
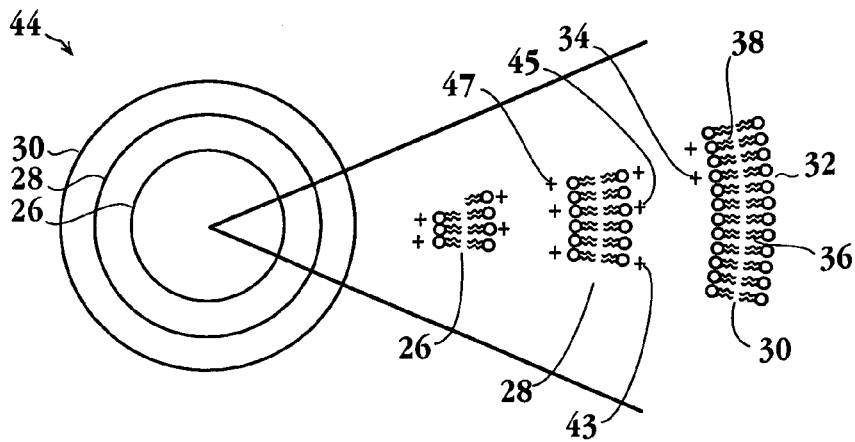

FIGS. 1B–1C are illustrations of multilamellar lipid vesicle, also prepared by the method to be described to yield an asymmetric outer lipid bilayer or coating. With initial reference to FIG. 1B, vesicle 24 has a plurality of nested, concentric lipid coating layers, indicated as idealized bilayers 26, 28, 30. In practice, the number of lipid bilayers may be many more than the three illustrated in the drawing and may be more complex in lipid arrangement than the simplified bilayer shown. A portion of the lipid coat, comprised of lipid bilayers 26, 28, 30, is shown in exploded view for ease of viewing the lipid arrangement. Lipid coating 30 is the outermost lipid layer and is in contact with the external medium in which the particles are suspended. Outer lipid coating 30 has an external surface 32 and an internal surface 34, where the external surface is defined by an outer lipid leaflet 36 and the internal surface defined by an inner lipid structure 38. Outer lipid leaflet 36 is distinct in its lipid composition relative to the lipid composition of inner lipid structure 38 in that the outer lipid leaflet has fewer charged lipids, and more preferably fewer cationic lipids. In contrast, the inner lipid structure includes cationic lipids that result in a positive surface charge along the internal surface 38, as indicated by the plus symbols at 40, 42. Thus, in the multilamellar lipid particle illustrated in FIG. 1B, the outer lipid coating is asymmetric with respect to its lipid composition.

FIG. 1C shows a lipid particle 44 similar to lipid particle 24 of FIG. 1B, and like elements are identified by like numerical identifies. Particle 44 includes a plurality of lipid layers, such as layers 26, 28, 30. Outer lipid coating 30 has an external surface 32 and an internal surface 34. In this embodiment, the lipid composition of outer lipid coating 30 is relatively constant between external surface 32 and internal surface 34, where the outer lipid coating has minimal charged lipids. The lipid layer internal from the outermost lipid coating 30, however, includes charged lipids in its composition as indicated by the plus symbols 43, 45, 47. Thus, in this embodiment of the lipid particle, the asymmetric lipid coating is with respect to the lipid composition of the outer lipid coating 30 to the inner lipid structure or lipid layers. That is, the lipid coating as a whole is asymmetric with respect to its lipid composition as it extends from the outer particle surface to the inner particle regions.

Figure 1D:
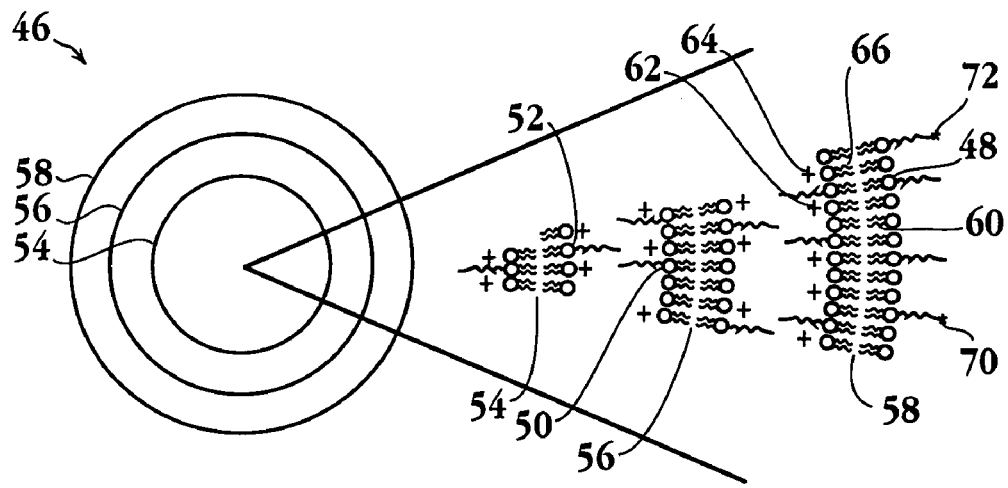

FIG. 1D shows another embodiment of a multilamellar lipid particle 46, similar to that described in FIG. 1B. Particle 46, however, includes a lipid derivatized with a hydrophilic polymer, such as lipids 48, 50, 52, which are representative of the derivatized lipids in each of the lipid bilayers, 54, 56, 58 shown in the drawing. As will be discussed below, particles having a polymer-derivatized lipid distributed across the particle's lipid coat are formed by including the polymer-derivatized lipid in the lipid mixture during particle formation. The outer lipid coating 58 in particle 46 has an asymmetric lipid composition due to the absence of charged lipids in outer lipid leaflet 60 and the presence of charged lipids, such as lipids 62, 64, in inner lipid structure 66. Presence of charged lipids in the inner lipid leaflet results in a charged inner lipid coating surface, as indicated by the plus symbols along the inner coating surface.

The lipid particle in FIG. 1D includes an additional feature that can optionally be included. The lipid particles can also be prepared to include targeting ligands, such as ligands 70, 72, that act as homing devices to bring the lipid particles to a desired site for therapeutic action. Targeting ligands attached to lipid particles are described, for example, in U.S. Pat. Nos. 5,891,468, 6,056,973 and 6,180,134, the disclosure of these patents with respect to moieties suitable for targeting ligands, preparation of lipid conjugates carrying the ligands, and preparation of lipid particles comprising lipid-ligand conjugates is incorporated by reference herein. Targeting ligands can be incorporated into lipid particles after formation by incubating the pre-formed lipid particles in a micellar solution of lipid-ligand or lipid-linker-ligand conjugates. Targeting ligands can also be incorporated into the lipid particles by including a lipid-ligand conjugate in the lipid composition for particle formation.

Figure 1E:
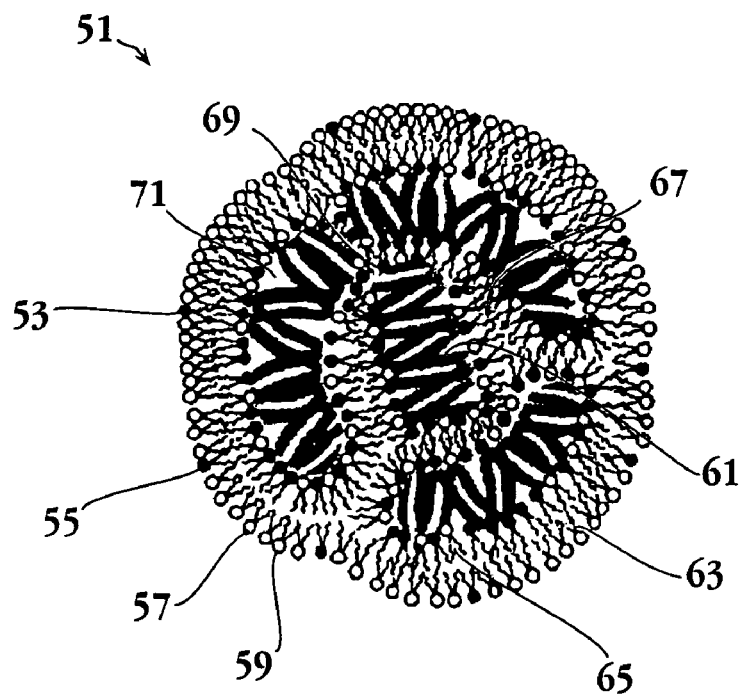

Another exemplary lipid particle is illustrated in FIG. 1E. As noted above, the illustrations in FIGS. 1A–1D are highly idealized, showing spherical particles, with defined lipid layers and defined aqueous spaces. In practice, the particles may be much more complex in structure, as partially illustrated in FIG. 1E. FIG. 1E shows a lipid-DNA particle 51 comprised of cationic lipids (denoted by a solid head group, such as lipids 53, 55) and neutral lipids (denoted by an open head group, such as lipids 57, 59). DNA 61 is disposed in the interior of the particle and via charge interaction is coated with more cationic lipids than with neutral lipids. The particle has a defined outer lipid leaflet 63 and an internal lipid structure comprised of the lipid layers internal to the outer lipid leaflet. The inner lipid structures thus include the inner leaflet 65 opposing outer leaflet 63 and the inner bilayers surrounding the DNA, such as bilayer 67, 69. Particle 51 has pockets of aqueous space, such as pocket 71, but does not have the defined aqueous internal compartment common in conventional liposomes.

A. Lipid Particle Preparation

As discussed above, particularly with respect to FIGS. 1B–1C, particles described herein have an asymmetric lipid coating with respect to either a single lipid layer in the particle (e.g., FIG. 1B where the lipid composition of the outer lipid layer is asymmetric) or with respect to the lipid coating as it extends from the outer particle surface to inner particle regions (FIG. 1C). Preparation of such asymmetric lipid particles will now be described.

Figure 2A:
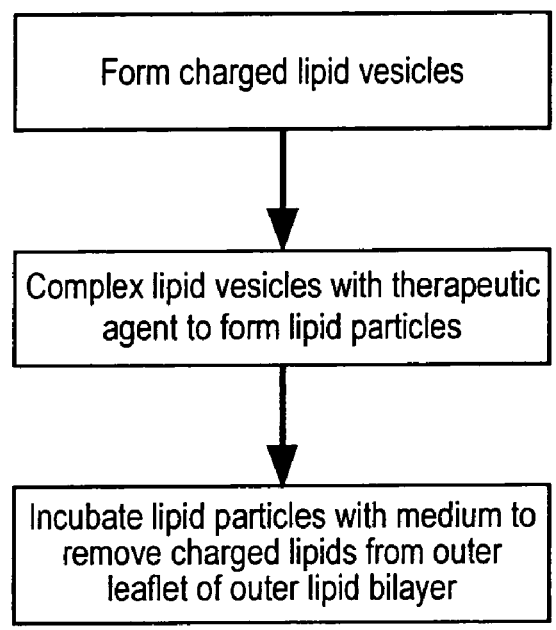
FIG. 2A is a flow chart schematic showing the steps for formation of lipid particles.
Figure 2B:
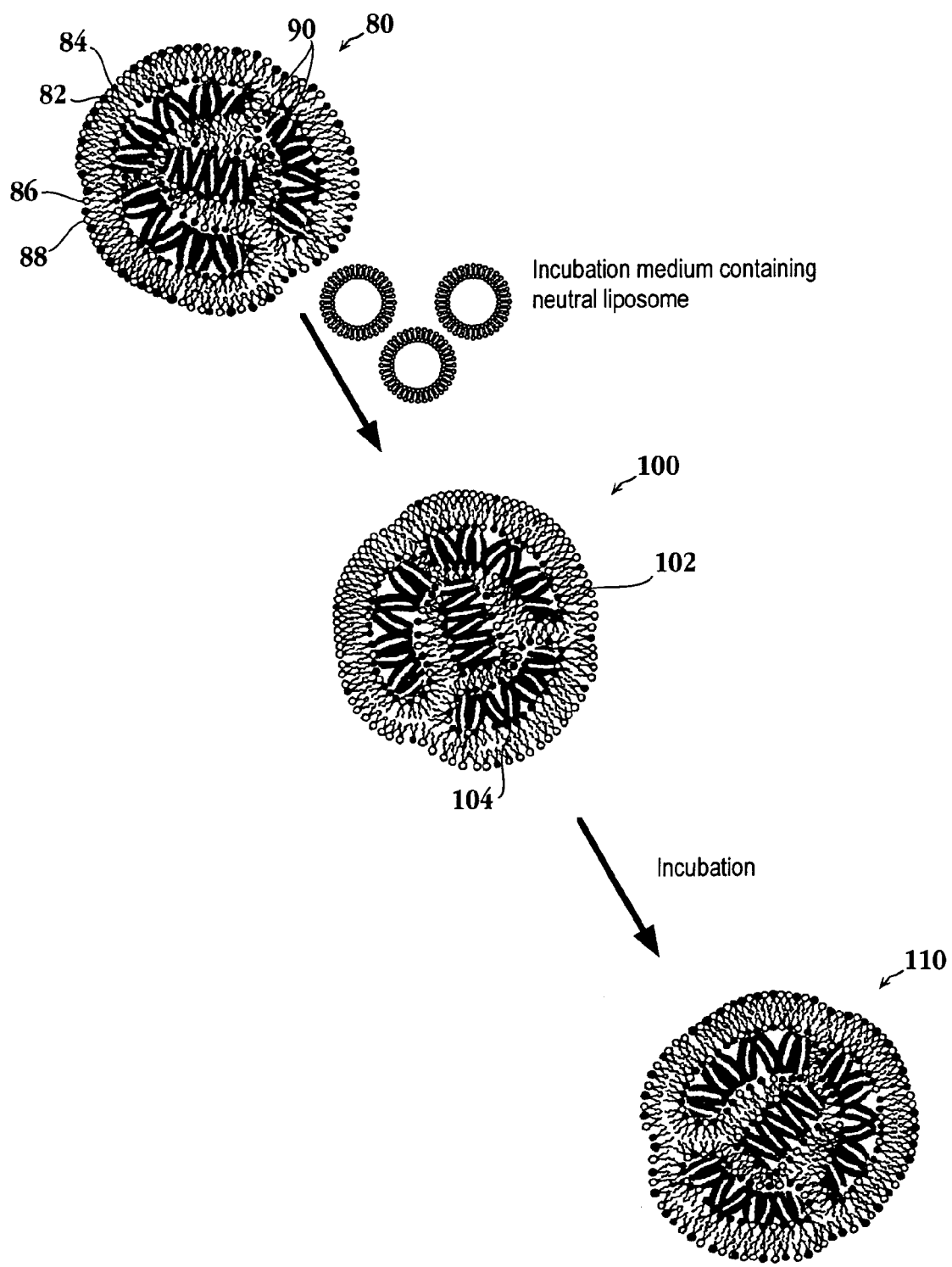
FIG. 2B is a schematic depiction of an exemplary lipid-DNA particle at each formation step.

Lipid particles having an asymmetric outer lipid coating are prepared according to a method illustrated in general terms in FIG. 2A, where a flow chart schematic of the basic steps involved in formation of the lipid particles is provided. FIG. 2B provides a schematic depiction of the nature of an exemplary lipid particle at each step in formation. In broad terms, the first step is to prepare lipid vesicles from a lipid composition that includes a charged lipid, such as a cationic lipid. Next, the lipid vesicles are mixed with a therapeutic agent, for complexation of the agent with the charged lipid vesicles, thereby forming lipid particles. An exemplary particle corresponding to this step is shown as particle 80 in FIG. 2B. Particle 80 is comprised of cationic lipids (denoted by a solid head group, such as lipids 82, 84) and neutral lipids (denoted by an open head group, such as lipids 86, 88). DNA 90 is disposed in the interior of the particle and via charge interaction is coated with more cationic lipids than with neutral lipids.

With continuing reference to FIG. 2A, the lipid particles are then incubated in a medium and under conditions that achieve extraction of charged lipids from the outer lipid coating or from the outer leaflet of the outermost lipid coating of the lipid particles. The nature of the lipid-DNA particle after incubation with an incubation medium comprising a suspension of neutral liposomes is shown as particle 100 in FIG. 2B. Incubation of the particle resulted in removal of cationic lipids from the outer lipid leaflet 102, as denoted in the schematic by fewer lipids with a solid head group relative to particle 80 prior to incubation. The difference in composition between the outer lipid leaflet and the inner lipid structures lends an asymmetric lipid composition to the particle. The asymmetric particle 100 has a reduced surface charge relative to particle 80 prior to incubation. In one embodiment of the invention, the incubation is sufficient to remove the charged lipids from the outer lipid leaflet and from the inner lipid structures abutting the outer lipid leaflet. In another embodiment, the incubation is performed in such a way, e.g. by varying the incubation time, temperature, and/or medium, to remove charged lipids primarily from the outer lipid leaflet. This latter embodiment is illustrated in the particle 110 in FIG. 2B, and will be discussed more fully below. In brief, in this latter embodiment, charged lipids are present in the inner lipid structure, such as lipid leaflet 104 of particle 100, and available for translocation or "flip-flop" to the outer lipid leaflet. The translocation is accomplished by incubating the particles at a temperature sufficient to permit movement of the lipids, typically at a temperature above the lipid composition's phase transition temperature. The higher concentration of charged lipids in the inner lipid layers permits translocation of the charged lipids to the region of lower concentration in the outer lipid leaflet. The translocation results in a regeneration of surface charge on the lipid-DNA particle, as illustrated in particle 110 by the increased presence of cationic lipids (represented by the solid polar head groups) relative to that in particle 100.

It is also possible to generate asymmetric lipid particles by first preparing the lipid vesicles having an asymmetric outer lipid coating and then complexing the asymmetric vesicles with a charged drug. In this embodiment, lipid particles comprised of a charged lipid are incubated under conditions suitable for removal of a majority of charged lipids from the outer lipid coating or leaflet, thus generating asymmetric vesicles. After formation of the asymmetric lipid coating, the asymmetric lipid vesicles are subsequently complexed with a drug to form asymmetric lipid-drug particles.

1. Preparation of Lipid Vesicles

Lipid vesicles, typically unilamellar or multilamellar liposomes, are prepared from a lipid composition that includes a charged lipid, preferably a cationic lipid. The cationic lipid can be the sole vesicle-forming lipid in the composition, or can be one of two or several lipids, vesicle-forming or non-vesicle-forming, in the composition. Exemplary unilamellar vesicles prepared in support of the invention were prepared from a lipid composition comprised of a cationic vesicle-forming lipid, neutral lipids, and a vesicle-forming lipid derivatized with a hydrophilic polymer.

A cationic vesicle-forming lipid is one having a polar head group with a net positive charge, at the operational pH, e.g., pH 4–9. Exemplary cationic lipids include 1,2-dioleIyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy) propyl]-N,N,N-trimethylammonium chloride (DOTMA); 1,2-dimyristoyl-3-trimethylammonium-propane (DMTAP); dioleoylphosphatidylcholine (DOPC); 3β[N-(N',N'-dimethylaminoethane) carbamoyl] cholesterol (DC-Chol); dimethyldioctadecylammonium (DDAB), cationic surfactants, sterol amines, and others. It is also possible to render a neutral or negatively charged lipid cationic by derivatization with a cationic moiety. For example, a phospholipid, such as phosphatidylethanolamine, can be derivatized at its polar head group with a positive moiety, e.g., lysine, as illustrated, for example, for the lipid DOPE derivatized with L-lysine (LYS-DOPE) (Guo, L. et al., *Journal of Liposome Research* 3(1):51–70 (1993)). Also included in this class of cationic lipids are the glycolipids, such as cerebrosides and gangliosides having a cationic polar head-group. Another cationic vesicle-forming lipid which may be employed is cholesterol amine and related cationic sterols.

It will be appreciated that the charged lipid included in formation of the lipid vesicles can be an anionic lipid, such as dimyristoyl phosphatidylglycerol (DMPG); dioleoylphosphatidylglycerol (DOPG); dioleoylphosphatidylethanolamine (DOPE); dioleoylphosphatidylcholine (DOPC); and others.

The lipid composition for preparation of the lipid vesicles, in addition to a charged lipid species, may include other lipids. Typically, the composition will include a vesicle-forming lipid, which intends a lipid that can form spontaneously into bilayer vesicles in an aqueous medium, as exemplified by the phospholipids. The lipid composition can also include lipids that are stably incorporated into lipid bilayers, with its hydrophobic moiety in contact with the interior, hydrophobic region of the bilayer membrane, and its head group moiety oriented toward the exterior, polar surface of the bilayer lipid membrane. Vesicle-forming lipids are preferably ones having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two hydrocarbon chains are typically between about 14–22 carbon atoms in length, and have varying degrees of unsaturation. Phospholipids with acyl chains having varying degrees of saturation can be obtained commercially or prepared according to published methods.

In one embodiment, the vesicle-forming lipid is selected to achieve a specified degree of fluidity or rigidity to control the conditions effective for insertion of a targeting lipid-ligand conjugate and/or to permit translocation of charged lipids from the inner lipid structure to the outer lipid leaflet upon in vivo administration of the lipid particles, as will be described. Lipid particles having a more rigid lipid coating are achieved by incorporation of a relatively rigid lipid, e.g., a lipid having a relatively high phase transition temperature, e.g., up to 60° C. Rigid, i.e., saturated, lipids contribute to greater membrane rigidity in the lipid coating. Other lipid components, such as cholesterol, are also known to contribute to membrane rigidity in lipid structures. Exemplary rigid lipids include distearyl phosphatidylcholine (DSPC), which has a phase transition temperature of 62° C., and hydrogenated soy phosphatidylcholine (HSPC), which has a phase transition temperature of 58° C.

A more fluid bilayer is achieved by incorporation of a relatively fluid lipid, typically one having a lipid phase with a relatively low liquid to liquid-crystalline phase transition temperature, e.g., at or below body temperature of about 37–38° C. Examples of lipids having a phase transition temperature below 38° C. are egg phosphatidylcholine (−15 to −7° C.), dimyristoylphosphatidylcholine (23° C.), 1-myristoyl-2-palmitoylphosphatidylcholine (27° C.), 1-palmitoyl-2-myristoylphosphatidylcholine (35° C.), dimyristoylphosphatidylglycerol (23° C.), brain sphingomyelin (32° C.) (Szoka, F. et al., *Ann. Rev. Biophys. Bioeng.*, 9:467 (1980)). Phase transition temperatures of many lipids are tabulated in a variety of sources, such as Szoka & Papahadjopoulos, *Ann. Rev. Biophys. Bioeng.*, 9:467–508 (1980), Avanti Polar Lipids catalogue, and Lipid Thermotropic Phase Transition Database (LIPIDAT, NIST Standard Reference Database 34).

As mentioned above with respect to FIG. 1D, the lipid particles can optionally include a surface coating of hydrophilic polymer chains and/or lipid-anchored targeting conjugates. Either of these features can be incorporated into the lipid particles by including a polymer-derivatized lipid and/or a ligand-derivatized lipid in the lipid composition used for formation of the lipid vesicles in the initial step of the method. It is also possible to incorporate these features into the lipid particles in the third step of the process, when the lipid particles are incubated in a medium. In this case, the polymer-derivatized lipid and/or a ligand-derivatized lipid is included in the incubation medium and becomes inserted into the outer lipid coating of the lipid particles during incubation. This so-called "insertion" method has been described in U.S. Pat. Nos. 5,891,468, 6,056,973, and 6,210,707.

Lipids derivatized with a hydrophilic polymer, and liposomes containing polymer-derivatized lipids have been described (U.S. Pat. Nos. 5,013,556; 5,395,619). Polymer-derivatized lipids incorporated into a lipid coating forms a surface coating of hydrophilic polymer chains around the lipid vesicle. The surface coating of hydrophilic polymer chains is effective to increase the in vivo blood circulation lifetime of the lipid particles when compared to lipid particles lacking such a coating. Vesicle-forming lipids suitable for derivatization with a hydrophilic polymer include any of those lipids listed above, and, in particular phospholipids, such as distearoyl phosphatidylethanolamine (DSPE).

Hydrophilic polymers suitable for derivatization with a vesicle-forming lipid include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and hydrophilic peptide sequences. The polymers may be employed as homopolymers or as block or random copolymers.

A preferred hydrophilic polymer chain is polyethyleneglycol (PEG), preferably as a PEG chain having a molecular weight between 500–10,000 Daltons, more preferably between 1,000–5,000 Daltons. Methoxy or ethoxy-capped analogues of PEG (e.g., mPEG) are also preferred hydrophilic polymers, commercially available in a variety of polymer sizes, e.g., 120–20,000 Daltons.

Preparation of vesicle-forming lipids derivatized with hydrophilic polymers has been described, for example in U.S. Pat. No. 5,395,619. Preparation of liposomes including such derivatized lipids has also been described, where typically, between 1–20 mole percent of such a derivatized lipid is included in the liposome formulation.

Lipids derivatized with targeting ligands have also been described (U.S. Pat. Nos. 5,891,468, 6,056,973, and 6,210,707). Targeting ligands are typically moieties that are part of a receptor-ligand binding pair, where the ligand of the pair is attached to the lipid particles to enable the particles to specifically bind to a particular target bearing its receptor pair. Exemplary ligands are set forth in U.S. Pat. No. 5,891,468, and are incorporated by reference herein. Particularly preferred ligands are those that upon binding to a cell receptor are internalized by the cell. Such ligands permit intracellular delivery of the lipid particles' contents.

2. Formation of Lipid Particles via Complexation of Lipid Vesicles with a Therapeutic Agent With continuing reference to FIG. 2, after formation of charged lipid vesicles, the vesicles are mixed with a therapeutic agent to form lipid particles. As used herein, "lipid vesicles" refers to lipid structures, which may be small or large unilamellar or multilamellar liposomes or may be lipid structures having less defined lipid layers. "Lipid particles" refers to the lipid vesicles complexed with a therapeutic agent, and more particularly with a charged therapeutic agent.

As noted above, the lipid vesicles include a charged lipid, to impart an overall charge to the vesicle. The overall charge can be negative, by inclusion of anionic lipids, or positive, by inclusion of cationic lipids. The therapeutic agent mixed with the charged lipid vesicles is also charged, and more specifically, carries a charge opposite to the charge of the lipid vesicles. Cationic lipid vesicles mixed with a negatively charged therapeutic agent complex to form lipid particles. Similarly, anionic lipid vesicles mixed with a positively charged therapeutic agent complex to form lipid particles.

Positively and negatively charged therapeutic agents are known in the art. A preferred negatively charged therapeutic agent is a nucleic acid, either DNA or RNA, single strand or double strand. In one embodiment, the nucleic acid is an antisense DNA oligonucleotide composed of sequences complementary to its target, usually a messenger RNA (mRNA) or a mRNA precursor. The mRNA contains genetic information in the functional, or sense, orientation and binding of the antisense oligonucleotide inactivates the intended mRNA and prevents its translation into protein. Such antisense molecules are determined based on biochemical experiments showing that proteins are translated from specific RNAs and that once the sequence of the RNA is known, an antisense molecule that will bind to it through complementary Watson-Crick base pairs can be designed. Such antisense molecules typically contain between 10–30 base pairs, more preferably between 10–25, and most preferably between 15–20. The antisense oligonucleotide can be modified for improved resistance to nuclease hydrolysis, as phosphorothioate, methylphosphonate, phosphodiester and p-ethoxy oligonucleotides (WO 97/07784).

Nucleic acids are useful as therapeutic agents for a variety of therapies, including, but not limited to, treatment of viral, malignant and inflammatory diseases and conditions, such as, cystic fibrosis, adenosine deaminase deficiency and AIDS. Treatment of cancers by administration of tumor suppressor genes, such as APC, DPC4, NF-1, NF-2, MTS1, RB, p53, WT1, BRCA1, BRCA2, VHL, or administration of oncogenes, such as PDGF, erb-B, erb-B2, RET, ras (including Ki-ras, N-ras), c-myc, N-myc, L-myc, Bcl-1, Bcl-2 and MDM2, are contemplated. Administration of the following nucleic acids for treatment of the indicated conditions are also contemplated: HLA-B7, tumors, colorectal carcinoma, melanoma; IL-2, cancers, especially breast cancer, lung cancer, and tumors; IL4, cancer; TNF, cancer; IGF-1 antisense, brain tumors; IFN, neuroblastoma; GM-CSF, renal cell carcinoma; MDR-1, cancer, especially advanced cancer, breast and ovarian cancers; Factor VIII, hemophilia, and HSV thymidine kinase, brain tumors, head and neck tumors, mesothelioma, and ovarian cancer.

In addition to nucleic acids, charged organic drug molecules are also suitable for complexing with the lipid vesicles. A variety of charged drugs are known in the art and readily recognized by those of skill.

3. Incubation of Lipid Particles to Create Asymmetric Outer Lipid Coating

With continuing reference to FIG. 2, after complexing the lipid vesicles with the therapeutic agent, the lipid particles are incubated under conditions effective to extract at least a portion of the charged lipids from the outer lipid coating layer or from the outer lipid leaflet of the outer lipid coating. As discussed above in FIG. 1, the lipid particles include an outer lipid coating comprised of an inner lipid structure and an outer lipid surface. The outer lipid surface or leaflet is in contact with the external, incubating, medium. The lipid particles are incubated to achieve removal of substantially all of the charged lipids from the outer leaflet or from the outermost lipid coating, thus rendering the outer lipid coating asymmetric. The extent of removal of the charged lipids is determined and controlled by such factors as incubation time, temperature, and medium, as will be further described.

Removal of the charged lipids from the outer lipid coating or leaflet is achieved by placing the lipid particles in a medium into which the charged lipids partition. The conditions to effect partitioning of the lipids from the particles into the medium are variable, and include selection of the incubation medium, temperature of the incubation medium, and time of incubation. In studies performed in support of the invention, an incubation medium comprised of an aqueous suspension of neutral lipid vesicles was effective to cause partitioning of cationic lipids from the outer lipid coating or leaflet of the particles' lipid coating. An incubation medium containing neutral lipid vesicles serves as a sink for the cationic lipids, causing movement of the cationic lipids from high concentration in the lipid particle outer coating to low concentration in the incubation medium. A preferred incubation medium contains the same neutral lipid present in the lipid particles, so that no substantial movement of neutral lipid from the particles to the incubation medium occurs. Other exemplary incubation media are those that include a negatively charged lipid, a surfactant, polymer particles, or other materials capable of drawing out a charged lipid from the lipid particles.

In another embodiment, after incubation of the lipid particles to reduce the cationic surface charge, the particles are subsequently incubated in a second medium that includes a negatively charged lipid species to introduce a negative charge to the outer lipid leaflet of the lipid particles.

As noted above, the lipid particles can optionally include a surface coating of hydrophilic polymer chains and/or lipid-anchored targeting conjugates. Polymer-derivatized lipids or ligand-derivatized lipids can be incorporated into the lipid particles by including one or both of these conjugates in the incubation medium. The conjugates insert into the outer lipid coating of the lipid particles during incubation. Insertion of a lipid-polymer conjugate and/or a lipid-targeting ligand conjugate during incubation of the lipid particles can be tailored according to the composition of the lipid bilayer, the targeting ligand, and other factors. For example, a rapid rate of insertion can be achieved by a higher incubation temperature, but must be balanced against the temperature to which the ligand can be safely heated without affecting its activity. The phase transition temperature of the lipids in the lipid composition will also dictate the temperature suitable for insertion. It will also be appreciated that insertion can be varied by the presence of solvents, such as amphipathic solvents including polyethyleneglycol and ethanol, or detergents.

B. Characterization of Lipid Particles

Lipid particles were prepared as described in Example 1. Briefly, cationic small unilamellar vesicles (SUVs) were prepared from a lipid composition of DMTAP, DOPE, cholesterol, and mPEG-DSPE. The cationic lipid vesicles were complexed with a DNA plasmid bearing a luciferase reporter gene to form lipid particles. Complexation of the cationic SUVs and the nucleic acid was done at a temperature of about 0° C. The lipid particles were separated from uncomplexed cationic SUVs and/or nucleic acid. Then, the lipid particles were incubated in an incubation medium comprised of neutral SUVs (POPC, cholesterol, and mPEG-DSPE) at a temperature of 4° C. for 24 hours. After incubation, the lipid particles, now with an asymmetric outer lipid bilayer, were isolated from the other lipid components in the incubation medium by sucrose density gradient ultracentrifugation for analysis of charge by zeta potential.

Figure 3:
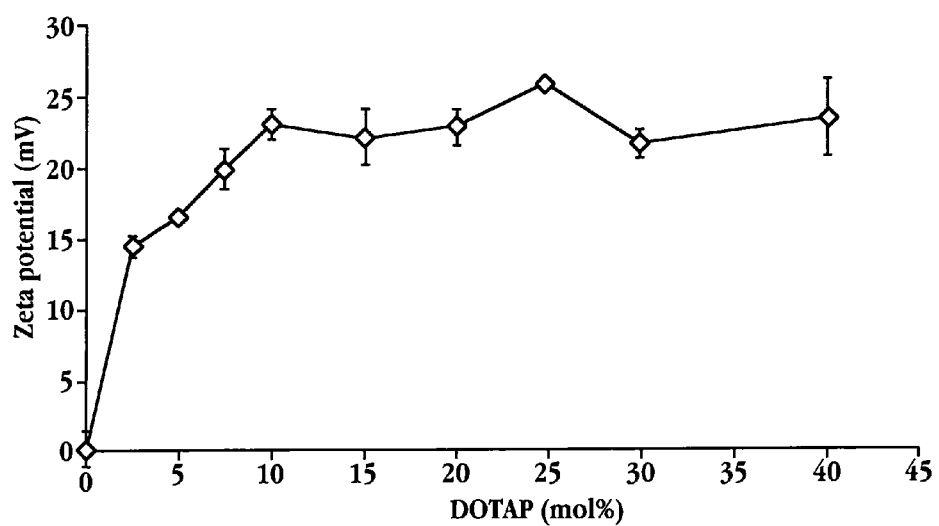
FIG. 3 is a graph of zeta potential, in mV, as a function of cationic lipid concentration (DOTPA, mole percent) for cationic liposomes.

Zeta potential values provide a measure of the apparent charge on the outer surface of the particles. More specifically, the zeta potential is a measure of the potential that arises across the interface between a liquid boundary layer in contact with a solid and the movable diffuse layer in the body of the liquid, e.g., the slipping plane. Zeta potential values were measured as set forth in the methods section below, using a commercially available apparatus. FIG. 3 shows the relationship between zeta potential, in mV, for cationic lipid vesicles comprised of DOTAP (x mol %), POPC (55-x mol %), cholesterol (40 mol %), and polyethylene glycol derivatized distearoyl (PEG-DS, 5 mol %), where the amount of DOTAP is indicated along the x-axis of the graph in mol %. The lipid vesicles were prepared at the compositions indicated and extruded to a size of about 100 nm. Zeta potential was measured in 5 mM NaCl at 25° C. The zeta potential increases as a function of concentration of cationic lipid, DOTAP, with a rapid increase in zeta potential observed as the concentration increases from 0–10 mole percent, and a slower increase for compositions having greater than 10 mole percent DOTAP.

In another study, lipid particles were prepared according to Example 1. The lipid composition consisted of DMTAP (50 mol %), DOPE (24 mol %), cholesterol (24 mol %), and PEG-DS (2 mol %). After complexing the lipid vesicles with DNA, but prior to incubation for generation of the asymmetric lipid coating, a sample of the lipid particles was reserved for zeta potential analysis as a comparative control. The remaining particles were incubated in a medium containing neutral lipid vesicles (Example 1) for various times to generate an asymmetric lipid coating. The asymmetric lipid particles were separated from the other lipid vesicles in the incubation medium using sucrose density gradient centrifugation and the zeta potential was measured. The results are shown in Table 1A, along with the size of the particles, determined by dynamic light scattering.

TABLE 1A

Zeta Potential of Lipid Particles and Asymmetric Lipid Particles Treated Under Various Conditions

| Lipid Particle | Particle Size at 90° (nm) | Zeta Potential (mV) |
| --- | --- | --- |
| lipid particle with no asymmetric lipid coat, control | 272 | 17.27 |
| lipid particle with asymmetric lipid coating formed by incubation in medium with neutral vesicles for 24 hr, 25° C. | 311 | 8.30 |
| lipid particle with asymmetric lipid coating formed by incubation in medium with neutral vesicles for 3.5 hr, 37° C. | 295 | 8.63 |

The zeta potential of the lipid particles with no asymmetric lipid coating was 17.27 mV, indicating a positive charge on the external surface of the particles. Incubation of the particles in an incubation medium containing neutral lipid vesicles for 24 hours at 25° C. and for 3.5 hours at 37° C. was effective to reduce the zeta potential to 8.30 mV and 8.63 mV, respectively, indicating the surface charge has been reduced significantly.

A similar study was conducted using lipid particles comprised of DMTAP (50 mol %), POPC (24 mol %), cholesterol (24 mol %), and PEG-DS (2 mol %). Zeta potential measurements were made on a sample of the lipid particles after complexing the lipid vesicles with DNA, but prior to incubation for generation of the asymmetric lipid coating, as a control. Particles were incubated in an incubation medium at different times and temperatures to generate an asymmetric lipid coating. The zeta potential measurements and size of the particles, determined by dynamic light scattering, are shown in Table 1B.

TABLE 1B

Zeta Potential of Lipid Particles and Asymmetric Lipid Particles Treated Under Various Conditions

| Lipid Particle | Particle Size at 90° (nm) | Zeta Potential (mV) |
|---|---|---|
| lipid particle with no asymmetric lipid coat, control | 299 | 23.07 |
| lipid particle with asymmetric lipid coating formed by incubation in medium with neutral vesicles for 24 hr, 25° C. | 349 | 4.50 |
| lipid particle with asymmetric lipid coating formed by incubation in medium with neutral vesicles for 3.5 hr, 37° C. | 294 | 7.23 |

Incubation of the lipid particles in a medium containing neutral lipid vesicles was effective to extract cationic lipids from the outer lipid leaflet, as evidenced by the decreased zeta potential in the asymmetric lipid particles relative to the control particles.

In summary, lipid particles having a charged lipid in the lipid coating composition were incubated in a medium to extract the charged lipid from the outer coating, as evidenced by the zeta potential measurements of the asymmetric lipid particles. The presence of the charged lipid during particle formation is advantageous in that charge-charge interaction between the lipid and the charged therapeutic agent permits efficient formation of the particles. Removal of the charged lipid from the outer lipid coating is advantageous in that upon in vivo delivery a reduced or absent surface charge permits a longer blood circulation time for a more widespread biodistribution.

To determine whether the lipid particles described above with respect to Tables 1A, 1B, and in Example 1 would remain uncharged after in vivo administration, the asymmetric lipid particles were placed in a 37° C. temperature for 15 hours, to simulate conditions after in vivo administration. The zeta potential of the particles was measured after the 15 hour period, and the results are shown in Tables 2A, 2B. Also, to determine the extent that the lipid coating surrounded and protected the entrapped DNA, a dye (PicoGreen® dsDNA quantitation reagent) that emits fluorescence when in contact with DNA was added to an aliquot of each preparation. The percent of DNA protection was determined by comparing the fluorescent emission of the lipid particles to that of naked DNA treated with the dye. The percent of DNA protection is also shown in Tables 2A, 2B.

TABLE 2A

Particle Size, Percent of DNA Protected, and Zeta Potential of Asymmetric Lipid Particles Treated Under Various Conditions

| Lipid Particle[1] | Particle Size at 90° (nm) | DNA Protection (%) | Zeta Potential (mV) |
|---|---|---|---|
| lipid particle with no asymmetric lipid coat, control | 272 | 93.8 | 17.27 |
| lipid particle with no asymmetric lipid coat, control, after in vivo simulation (15 hr, at 37° C.) | 319 | — | 25.93 |
| lipid particle with asymmetric lipid coating formed by incubation in medium with neutral vesicles for 24 hr, 25° C. | 311 | 82.4 | 8.30 |
| lipid particle with asymmetric lipid coating formed by incubation in medium with neutral vesicles for 24 hr, 25° C., after in vivo simulation (15 hr, at 37° C.) | 314 | — | 9.63 |
| lipid particle with asymmetric lipid coating formed by incubation in medium with neutral vesicles for 3.5 hr, 37° C. | 295 | 81.0 | 8.63 |
| lipid particle with asymmetric lipid coating formed by incubation in medium with neutral vesicles for 3.5 hr, 37° C., after in vivo simulation (15 hr, at 37° C.) | 291 | — | 9.73 |

[1]Lipid particles prepared from a lipid composition of DMTAP/DOPC/cholesterol/mPEG-DS (50/24/24/2).

TABLE 2B

Particle Size, Percent of DNA Protected, and Zeta Potential of Asymmetric Lipid Particles Treated Under Various Conditions

| Lipid Particle[1] | Particle Size at 90° (nm) | DNA Protection (%) | Zeta Potential (mV) |
|---|---|---|---|
| lipid particle with no asymmetric lipid coat, control | 299 | 97.2 | 23.07 |
| lipid particle with no asymmetric lipid coat, control, after in vivo simulation (15 hr, at 37° C.) | 432 | — | 26.37 |

TABLE 2B-continued

Particle Size, Percent of DNA Protected, and Zeta Potential of Asymmetric Lipid
Particles Treated Under Various Conditions

| Lipid Particle[1] | Particle Size at 90° (nm) | DNA Protection (%) | Zeta Potential (mV) |
|---|---|---|---|
| lipid particle with asymmetric lipid coating formed by incubation in medium with neutral vesicles for 24 hr, 25° C. | 349 | 78.4 | 4.50 |
| lipid particle with asymmetric lipid coating formed by incubation in medium with neutral vesicles for 24 hr, 25° C., after in vivo simulation (15 hr, at 37° C.) | 329 | — | 4.40 |
| lipid particle with asymmetric lipid coating formed by incubation in medium with neutral vesicles for 3.5 hr, 37° C. | 294 | 78.7 | 7.23 |
| lipid particle with asymmetric lipid coating formed by incubation in medium with neutral vesicles for 3.5 hr, 37° C., after in vivo simulation (15 hr, at 37° C.) | 307 | — | 7.40 |

[1]Lipid particles prepared from a lipid composition of DMTAP/POPC/cholesterol/mPEG-DS (50/24/24/2).

The zeta potential of lipid particles having cationic lipids in the outer lipid leaflet (control particles) increased during the in vivo simulation conditions, indicating the increased presence of charge on the outer particle surfaces. The zeta potential of asymmetric lipid particles had no significant change after exposure to the in vivo simulation conditions of 15 hours at 37° C. For example, asymmetric lipid particles comprised of DMTAP, DOPE, cholesterol, and mPEG-DS (Table 2A) had a zeta potential of 8.30 mV after formation. That the zeta potential of the particles changed very little upon incubation at 37° C. suggests that the initial incubation at 25° C. for 24 hours or at 37° C. for 3.5 hours was sufficient to remove the cationic lipids from the outer lipid coating.

The ability of the asymmetric lipid particles to transfect cells in vitro was evaluated. The lipid particle compositions described above were contacted with cells in vitro according to the procedure described in Example 2. Luciferase expression of the cells was determined as an indication of transfection. Tables 3A and 3B show the luciferase expression of cells transfected with asymmetric particles prepared as described in Example 1.

TABLE 3A

Luciferase Expression after in vitro transfection of a luciferase-encoding plasmid entrapped in Asymmetric Lipid Particles Treated Under Various Conditions

| Lipid Particle[1] | Particle Size at 90° (nm) | Zeta Potential (mV) | Luciferase Expression (pg/mg) |
|---|---|---|---|
| lipid particle with no asymmetric lipid coat, control | 272 | 17.27 | 98,778 |
| lipid particle with no asymmetric lipid coat, control, after in vivo simulation (15 hr, at 37° C.) | 319 | 25.93 | 755,671 |
| lipid particle with asymmetric lipid coating formed by incubation in medium with neutral vesicles for 24 hr, 25° C. | 311 | 8.30 | 3,274 |
| lipid particle with asymmetric lipid coating formed by incubation in medium with neutral vesicles for 24 hr, 25° C., after in vivo simulation (15 hr, at 37° C.) | 314 | 9.63 | 1,319 |
| lipid particle with asymmetric lipid coating formed by incubation in medium with neutral vesicles for 3.5 hr, 37° C. | 295 | 8.63 | 981 |
| lipid particle with asymmetric lipid coating formed by incubation in medium with neutral vesicles for 3.5 hr, 37° C., after in vivo simulation (15 hr, at 37° C.) | 291 | 9.73 | 1,757 |

[1]Lipid particles prepared from a lipid composition of DMTAP/DOPC/cholesterol/mPEG-DSPE (50/24/24/2).

TABLE 3B

Luciferase Expression after in vitro Transfection of a Luciferase-Encoding Plasmid
Entrapped in Asymmetric Lipid Particles Treated under Various Conditions

| Lipid Particle[1] | Particle Size at 90° (nm) | Zeta Potential (mV) | Luciferase Expression (pg/mg) |
|---|---|---|---|
| lipid particle with no asymmetric lipid coat, control | 299 | 23.07 | 146,957 |
| lipid particle with no asymmetric lipid coat, control, after in vivo simulation (15 hr, at 37° C.) | 432 | 26.37 | 206,723 |
| lipid particle with asymmetric lipid coating formed by incubation in medium with neutral vesicles for 24 hr, 25° C. | 349 | 4.50 | 739 |
| lipid particle with asymmetric lipid coating formed by incubation in medium with neutral vesicles for 24 hr, 25° C., after in vivo simulation (15 hr, at 37° C.) | 329 | 4.40 | 274 |
| lipid particle with asymmetric lipid coating formed by incubation in medium with neutral vesicles for 3.5 hr, 37° C. | 294 | 7.23 | 120 |
| lipid particle with asymmetric lipid coating formed by incubation in medium with neutral vesicles for 3.5 hr, 37° C., after in vivo simulation (15 hr, at 37° C.) | 307 | 7.40 | 147 |

[1]Lipid particles prepared from a lipid composition of DMTAP/DOPC/cholesterol/mPEG-DSPE (50/24/24/2).

Tables 3A and 3B show that the asymmetric lipid particles have a reduced ability to transfect relative to the control particles that bear a positive surface charge. The lower transfection rate provides further evidence of the reduced surface charge on the asymmetric lipid particles.

In summary, the data in Table 1A–1B, 2A–2B, and 3A–3B illustrate a first aspect of the invention where a lipid particle composition is prepared from a charged lipid, and the particles are incubated to reduce the surface charge, relative to the surface charge prior to incubation. The particles are formed under conditions where a substantial portion of the charged lipids are removed from the outer lipid coating. The particles have a reduced charge relative to particles of the same lipid composition but untreated for removal of all or a portion of charged lipids from the outer lipid coating.

In another aspect, the invention provides an asymmetric lipid particle that has low or minimal surface charge after formation, but is able to regain or generate an external surface charge after exposure to in vivo conditions. This aspect was discussed briefly above with respect to particle 110 in FIG. 2B. After distribution of lipid particles in vivo, the presence of a surface charge can be beneficial. For example, after distribution and entry into a tumor, the presence of a surface charge to cause binding of the lipid particles with cell membranes would be desirable. Lipid particles that have an asymmetric lipid coating, where the outer lipid leaflet of the coating is uncharged and the inner lipid structure is charged after asymmetric lipid particle formation, prepared as described above, are capable of translocation of the cationic lipids after particle formation. Due to the concentration gradient of charged lipids in the lipid particle, where a higher concentration of charged lipids is present in the interior of the particle than on the external surface of the particle, a gradual transfer of the charged lipid occurs at body temperature. The gradual transfer, or translocation, of charged lipid from the inner lipid structures to the outer lipid leaflet was demonstrated in various studies, now to be described.

In this aspect of the invention, a lipid particle composition is provided where the lipid particles are prepared from a charged lipid, but the particles have no appreciable surface charge at a first temperature, typically a temperature lower than the phase transition temperature of the lipid coating. Yet, after exposure to a temperature higher than the phase transition of the lipid coating, the particles have a measurable surface charge. Translocation of the charged lipids from the inner lipid structures to the outer lipid leaflet was discussed above with respect to FIG. 2B and is illustrated by particles 100, 110 in FIG. 2B. With respect to the particles prepared for the study in Tables 2A, 2B, the lipid composition was comprised of 50 mole percent DMTAP which has a gel-liquid crystalline phase transition (Tc) of between about 20–24° C. (Zelphati et al., *Proc. Natl. Acad. Sci. USA*, 93:11493 (1996)). DMTAP is thus characterized as a fluid lipid, and the addition of cholesterol makes the lipid composition more rigid. DOPE at temperature above about 11° C. is in a hexagonal phase. Incubation of the particles at 37° C. is expected to bring the DMTAP/DOPE/cholesterol/mPEG-DS composition above its phase transition, where the lipids are fluid. Translocation of lipids from one lipid leaflet to another readily occurs when the lipids are in this fluid state above their phase transition. Thus, the asymmetric particles which have no appreciable charge after formation become charged when the lipids in the lipid coating are brought to a temperature above their phase transition, as evidenced, for example, by zeta potential measurements.

Figure 4A:
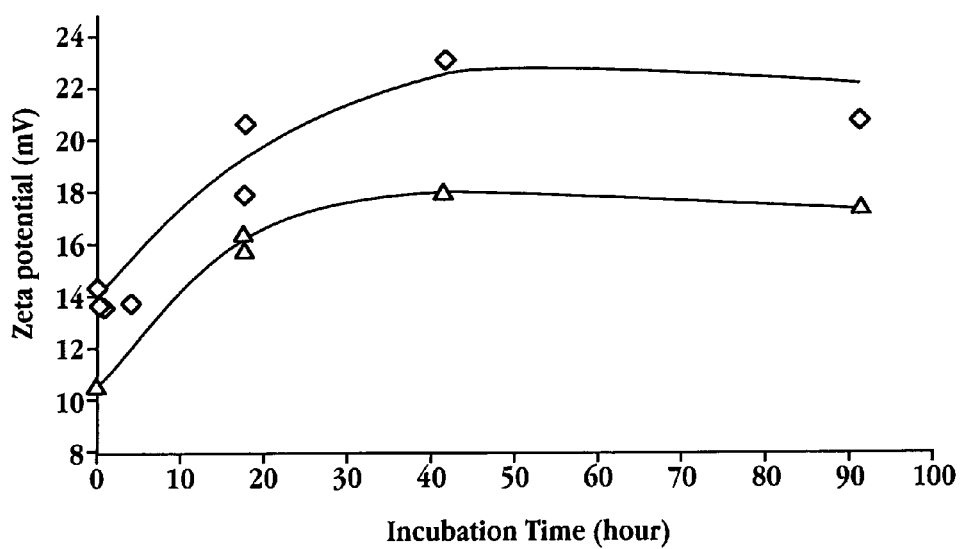
FIG. 4A is a graph of zeta potential, in mV, of asymmetric lipid particles comprised of DMTAP/DOPE/cholesterol/mPEG-DS (50:24:24:2) as a function of incubation time, in hours, at 37° C. in a buffer (diamonds) and in buffer containing neutral lipid vesicles (triangles)
Figure 4B:
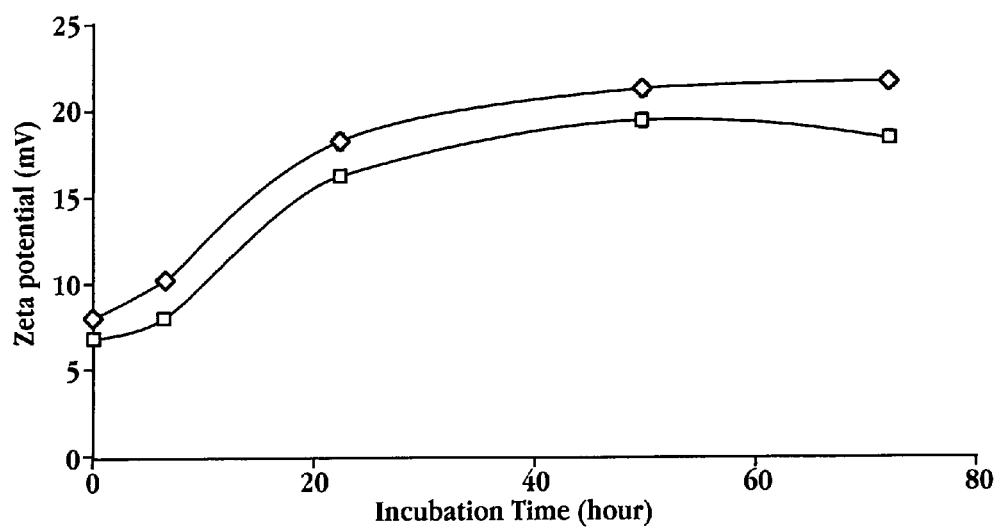
FIG. 4B is a graph of zeta potential, in mV, of asymmetric lipid particles comprised of DMTAP/DOPE/cholesterol/mPEG-DS (50:25.5:22.5:2) as a function of incubation time, in hours, at 37° C., in a buffer (diamonds) and in buffer containing neutral lipid vesicles (triangles)

Translocation of cationic lipids from the inner lipid leaflet to the outer lipid leaflet is illustrated in FIGS. 4A–4B. Lipid particles were prepared as described in Example 3 to have a lipid coating of DMTAP/DOPE/cholesterol/mPEG-DS (50:24:24:2), and were rendered asymmetric by incubation for 24 hours at 0–4° C. in a medium comprised of neutral lipid vesicles having a lipid composition of DOPE/cholesterol/mPEG-DS. The asymmetric lipid particles were then held at 37° C. for up to 90 hours, and at selected times, a sample was taken for zeta potential measurements. The medium in which the asymmetric lipid particles were incubated at 37° C. was water alone or was a suspension of neutral lipid vesicles formed of POPC/cholesterol/mPEG-DS (58:40:2). The zeta potential measurements as a function of incubation time, in hours, are shown in FIG. 4A. The asymmetric lipid particles incubated in the medium containing neutral lipid vesicles (triangles) had an initial zeta potential of about 11 mV. After incubation at 20 hours at 37° C., the zeta potential increased to about 16 mV. By 42 hours of incubation, the zeta potential had increased to 18 mV, with no further increase observed. Asymmetric lipid particles incubated in buffer alone (diamonds) also showed an increase in zeta potential over the incubation period, indicating translocation or "flip-flop" of cationic lipids from the inner to outer lipid leaflets.

FIG. 4B is a similar graph for asymmetric lipid particles of a slightly different lipid composition; DMTAP/DOPE/cholesterol/mPEG-DS (50:25.5:22.5:2). Here, asymmetric lipid particles incubated in the presence of neutral lipid vesicles (squares) increased in zeta potential over the 75 hour incubation period. A similar result was observed for the asymmetric lipid particles incubated in buffer alone (diamonds).

Figure 5:
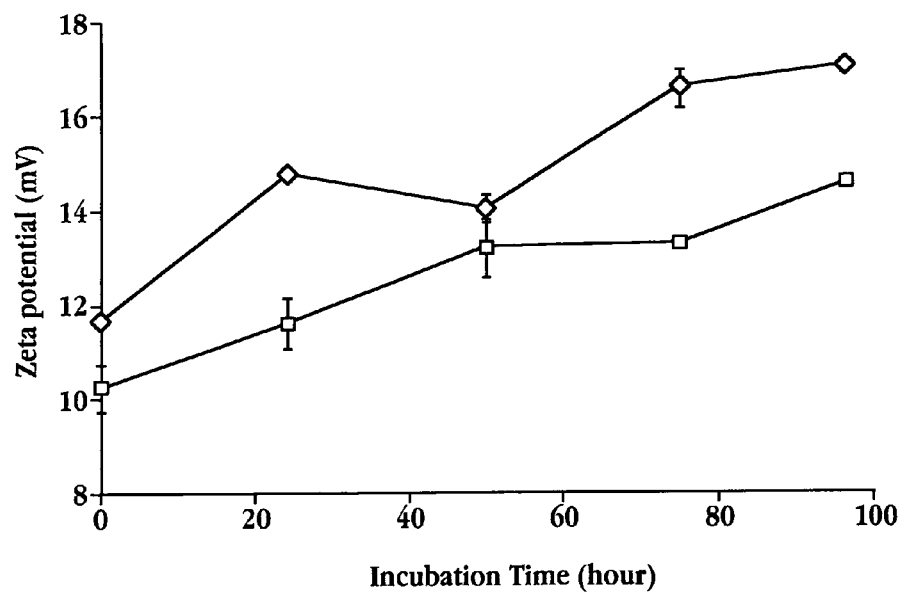
FIG. 5 is a graph of zeta potential, in mV, of asymmetric lipid particles comprised of DMTAP/DOPE/cholesterol/mPEG-DS (50:25.5:22.5:2) and stored at 4° C. for two months, as a function of incubation time, in hours, at 37° C., in a buffer (diamonds) and in buffer containing neutral lipid vesicles (squares)

The stability of the asymmetric lipid particles was analyzed in another study. Lipid particles prepared as described in Example 1 were prepared and stored at 4° C. for two months. After the two month storage, the particles were held in a medium at 37° C., with and without neutral lipid vesicles, for about 100 hours. The zeta potential of the asymmetric lipid particles was evaluated over the 100 hour incubation time to monitor translocation of cationic lipid from the inner to outer lipid leaflet. The results are shown in FIG. 5.

The zeta potential of asymmetric lipid particles increased over the incubation time, when incubated in buffer alone (diamonds) or in buffer containing neutral lipid vesicles (squares). The increase in zeta potential is indicative of movement of cationic lipids from the inner leaflet to the outer leaflet, showing that the asymmetric lipid coating was stable during the 2 month storage period.

An in vitro transfection study was conducted an asymmetric lipid particles that had been stored at 4° C. for two months. An asymmetric lipid particle composition comprised of DMTAP/DOPE/cholesterol/mPEG-DS (50:24:24:2) was prepared as described in Example 1. The asymmetric lipid particles were then held at 4° C. for two months. A control composition was prepared comprised of the same lipids, but which was not subjected to the incubation set to generate an asymmetric lipid bilayer. The control composition was also stored at 4° C. for two months. After storage, the two formulations were incubated at 37° C. Samples of the formulations after 37° C. incubation of 0 hours, 48 hours, and 60 hours were contacted with cells in vitro and luciferase expression measured. The results are shown in FIG. 6.

Figure 6:
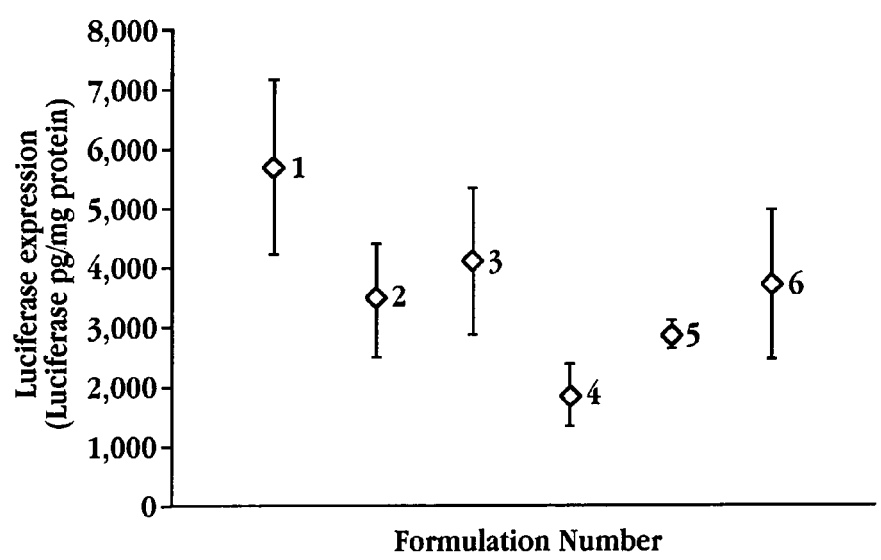
FIG. 6 is a graph showing luciferase expression in cells, in pg/mg protein, for six lipid particle formulations composed of DMTAP/DOPE/cholesterol/mPEG-DS (50:25.5:22.5:2), where Formulations 1–3 are control particles with no asymmetric bilayer and Formulations 4–6 are lipid particles having an asymmetric outer bilayer, where all formulations were incubated at 37° C. prior to transfection for times of 0 hours (Formulations 1, 3), 48 hours (Formulations 2, 5) and 60 hours (Formulations 3, 6).

In FIG. 6, formulation numbers 1, 2, and 3 correspond to the control lipid particles that lack an asymmetric lipid coating. Formulation numbers 4, 5, and 6 correspond to asymmetric lipid particles. Formulations 1 and 4 show the luciferase expression prior to incubation at 37° C. (0 hours incubation at 37° C.). The asymmetric lipid particle has a lower luciferase expression, thus a lower transfection ability, due to the absence of positive charge on the outer particle surface. Formulations 2 and 5 correspond to the control formulation and the asymmetric lipid particle formulation after incubation at 37° C. for 48 hours. The luciferase expression of Formulation 5 has increased relative to that of Formulation 4 due to translocation of cationic lipids from the inner leaflet to the outer leaflet during the 48 hour incubation period, which simulates in vivo conditions. Formulations 3 and 6 correspond to the control formulation and the asymmetric lipid particle formulation after incubation at 37° C. for 60 hours. The luciferase expression of Formulation 6 has increased relative to that of Formulations 4 and 5 due to further translocation of cationic lipids from the inner leaflet to the outer leaflet during the 60 hour incubation period. The luciferase expression of the control formulations 2 and 3 decreased as a result of incubation at 37° C.

The data presented in FIG. 6 shows that the asymmetric lipid particle composition has a low rate of transfection initially, due to the absence of charge on the particle surface. Exposure of the particles to a temperature close to, at, or above the phase transition temperature of the lipid composition allows for translocation, or "flip-flop" of charged lipids from the inner lipid leaflet to the outer lipid leaflet, generating a surface charge on the asymmetric lipid particles. Presence of the charge improves transfection since the charge enhances binding between the particles and the cells.

III. EXAMPLES

The following examples further illustrate the invention described herein and are in no way intended to limit the scope of the invention.

Methods

Measurement of Zeta potential: The zeta potential values of cationic liposomes and lipid-DNA particles were measured by Zetasizer 2000 (Malvern Ins.). Specifically, 50$\mu$L of liposomes was added to 5 mL aqueous solution containing 5 mM NaCl (made from 30 fold dilution of USP saline with Milli-Q water) and injected into the sample chamber according to the procedure give by the instrument vendor. Three measurements were made for each sample at 25° C.

Dynamic Light Scattering: Lipid particle sizes were determined were obtained by dynamic light scattering (DLS) using a Coulter N4MD instrument, operated according to the manufacturer's instructions. The results were expressed as the mean diameter in nm and standard deviation of a Gaussian distribution of particles by relative volume.

Example 1

Preparation of Asymmetric Lipid Particles

Cationic liposomes (small unilamellar vesicles) were prepared from a lipid composition of DMTAP/DOPE/CHOL/PEG-DS (50/24/24/2 mol/mol). Individual lipid stocks were made in chloroform/methanol (90:10 v/v) at 10 mg/mL for DMTAP (Avanti Polar Lipids, 890860, 20 mg/mL for DOPE (Avanti Polar Lipids, 850725), 20 mg/mL for cholesterol, and 10 mg/mL for mPEG-DS (methoxy-polyethyleneglycol-distearoyl, mPEG molecular weight 2000 Daltons, Shearwater Polymers Inc). Aliquots of solvent solutions containing appropriate amount of lipids for a final lipid suspension of 2 mL at 20 mM lipid concentration were taken using positive displacement pipettes and mixed in 10 mL round bottom flasks. The solvent was slowly removed by rotary evaporation at about 45° C. to form a thin film around the flask. The residual solvent was removed by vacuum overnight. The lipid was then hydrated by adding 2 mL of deionized water at 50° C. for 0.5–1 hour with stirring. The lipid suspension was then subject to extrusion through a Lipex® extruder (10 mL volume, Northern Lipids, Inc.) with double polycarbonate filters (0.8 µm over 0.1 µm) for 10 passes at 50° C. The final liposome diameter was 117±30 nm as measured by Coulter submicron particle sizer (model N4MD). After the extrusion, 2 mL deionized water was added into the extruder and was pushed through the filter to rinse off the remaining liposomes. This rinse was mixed with the liposomes to a final volume of 4 mL. The final lipid concentration was approximately 10 mM.

A. Preparation of neutral liposomes for incubation

Neutral liposomes with a composition of POPC/DOPE/CHOL/PEG-DS (58/40/2 mol/mol) were prepared by a procedure similar to that given in 1. above. The solvent stock solution was made at 40 mg/mL POPC (Avanti Polar Lipids, 850457). The final lipid concentration was 47.1 mM and the particle mean diameter was 108±40 nm.

B. Preparation of Lipid-plasmid DNA Complex

A DNA plasmid (pCC-luciferase) at 1 mg/mL concentration in water was slowly injected into the cationic liposome suspension (10 mM of neutral lipid/DOPE/cholesterol/mPEG-DS, 50/24/24/2 mol/mol, as prepared in Example 1, where the neutral lipid was either DOPE or POPC) set in an ice-water container. The DNA injection was performed using an infusion pump set at a rate of 10 µL/min with constant stirring. The final volume of the complexes was 1.6 mL with DNA concentration of 0.5 mg/mL and lipid concentration of 5 mM, i.e the DNA/lipid ratio of 1 µg per 20 nmoles lipid.

C. Preparation of Asymmetric Lipid-DNA Particles

The asymmetric lipid-DNA complexes were prepared by mixing lipid-DNA complex particles with 10 fold excess neutral liposomes ("sink liposomes") prepared as described in A. above. Specifically, 1.28 mL of the lipid-DNA complexes prepared as in B. above containing 6.4 µmoles lipids was mixed slowly with 2 mL neutral incubation liposomes (POPC/CHOL/mPEG-DS, 58/40/2 mol/mol) containing 64 µmoles lipids. The mixtures were set in an ice-water bath before incubation under various conditions as shown in FIGS. 4–6.

After the completion of the incubation, the sink liposomes were then separated by a sucrose density gradient centrifugation method. Specifically, a step-gradient of sucrose was loaded in clear ultracentrifugation tubes (4.0 mL 11×60 mm, Beckman cat 344062 for SW 60 Ti rotor). The gradients were 25, 20, 15, 10, and 5 wt % sucrose (bottom to top). The amount of samples loaded was typically 0.8–1 mL. The centrifugation was typically done at 40,000 rpm for 3 hour at 20° C. The lipid-DNA complexes were typically located in a weak band at the 10–15% interface. The sink liposomes were usually retained above the 10% sucrose region. The DNA complex band was then carefully removed using a pipette. For the preparation of a large volume of the asymmetric lipid-DNA particles, 40 mL centrifugation tubes were used with rotor SW28 (Beckman). The volume of sample loaded onto the tube was 4 mL. The centrifugation took typically 15–20 hour at 40,000 rpm at 20° C.

The final DNA concentration in the asymmetric lipid-DNA particles was determined by a fluorescent assay using PicoGreen® dsDNA quantitation reagent (Molecular Probes, P-7581). The standard curve was generated from a series of plasmid DNA solutions up to 2000 ng/mL DNA (pCC-Luc) in 10 mM Tris HCl and 1 mM EDTA at pH 7.0. The linear range was found up to 1000 ng/mL.

Example 2

In vitro Transfection

Asymmetric lipid-DNA particles and various controls prepared as described in Example 1 were compared in vitro. BHK cells were seeded in 6-well plates at 1.13×104 cells/well and incubated at 37° C., 5% CO2, for 48 hours with complete MEM media. Before the transfection, the cells were rinsed twice with 1.0 mL serum-free MEM media. An aliquot of the transfection sample was mixed with serum-free MEM media to achieve a desired concentration of plasmid DNA (typically 60–200 µg/mL pCC-Luc). For transfection, 1 mL was than overlayed onto the rinsed cells followed by incubation at 37° C. for 5 hours. After incubation, the sample-containing media was aspirated and replaced with 1.0 mL of complete MEM media and the incubation was continued under the same condition for an additional 16.5 hours.

The luciferase activity was assayed using Promega Luciferase Assay System (cat# E1500). The cells were rinsed twice with phosphate buffered saline (PBS) and then 250 µL of Cell Culture Lysis 1× Reagentlysis was added. The lysed cells were transferred to microcentrifuge tubes after two 8 minute incubations (with swirling the plates) at room temperature. Then the tubes were spun 14K for 10 minutes. Luciferase activity was assayed immediately using 20 µL of the sample by a luminometer (100 µL of luciferin and ATP containing assay buffer, 10 second measurement). The relative light unit was normalized by the amount of protein in the extracts.

The protein content was assayed using the BioRad protein reagent. Ten microliters of lysed cells was transferred onto 96 well flat bottom plate and added with 200 µL of reagent. Absorbance at 595 nm was measured using a Molecular Devices plate reader.

Example 3

Preparation of Asymmetric Lipid Particles

Lipid particles were formed as described in Example 1, except that the temperature of the incubation solution comprised of neutral SUVs (see step C in Example 1) was maintained between 0–4° C. with an ice bath.

Although the invention has been described with respect to particular embodiments, it will be apparent to those skilled in the art that various changes and modifications can be made without departing from the invention.

The invention claimed is:

1. A method of preparing lipid particles having an external lipid coating, comprising:
    preparing lipid particles comprised of (i) a lipid composition containing a charged lipid and (ii) a therapeutic agent, said particles each having an outer lipid coating having an external lipid leaflet and an internal lipid structure; and
    incubating said particles in a medium and under conditions effective to remove said charged lipid from the external lipid leaflet into said medium.

2. The method of claim 1, wherein said preparing is comprised of preparing lipid particles composed of a lipid composition containing at least one cationic lipid.

3. The method of claim 1, wherein said preparing comprises (i) forming lipid vesicles composed of said lipid composition and (ii) complexing said lipid vesicles with said therapeutic agent.

4. The method of claim 1, wherein said incubating comprises incubating said lipid particles in a medium containing uncharged lipid vesicles.

5. The method of claim 4, wherein said incubating further includes adding to the medium a lipid-polymer-ligand conjugate.

6. The method of claim 1, wherein said lipid particles are liposomes.

7. The method of claim 6, wherein said incubating further includes adding to the medium a lipid derivatized with a hydrophilic polymer.

8. The method of claim 7 wherein said adding is comprised of adding a phospholipid derivatized with polyethyleneglycol.

9. The method of claim 1, wherein said incubating is at a temperature of less than about 15° C.

10. The method of claim 1, wherein said incubating is for a time of greater than about 5 hours.

11. The method of claim 1, wherein said preparing is comprised of preparing lipid particles having an entrapped therapeutic agent selected from the group consisting of a charged drug, a protein, a peptide, and a nucleic acid.

12. The method of claim 11, wherein said therapeutic agent is a protein or peptide.

13. A method of preparing lipid particles having an asymmetric charged lipid composition in its outer lipid coating prior to in vivo administration, comprising:

preparing lipid particles comprised of (i) a lipid composition containing a charged lipid and (ii) a therapeutic agent, said particles each having an outer lipid coating having an external lipid leaflet and an internal lipid structure; and incubating said particles in a medium and under conditions effective to remove charged lipids from the external lipid leaflet into said medium.

14. The method according to claim 13, wherein said incubating includes incubating at a temperature of less than about 15° C.

15. The method according to claim 13, wherein said incubating includes incubating for a time of greater than about 5 hours.

16. The method according to claim 13, wherein said incubating includes incubating in a medium comprised of neutral lipid vesicles.

17. The method according to claim 13, further comprising separating the lipid particles from said medium.

18. The method of claim 1, further comprising separating the lipid particles from said medium.

* * * * *